US012521062B2

(12) United States Patent
Skelly et al.

(10) Patent No.: US 12,521,062 B2
(45) Date of Patent: Jan. 13, 2026

(54) PRESSURE SENSING COMPRESSION GARMENT

(71) Applicant: The Board of Regents of the Nevada System of Higher Education on Behalf of the University of Nevada, Las Vegas, Las Vegas, NV (US)

(72) Inventors: James Skelly, Stanford, CA (US); Francisco Mata Carlos, Las Vegas, NV (US); John Menezes, Las Vegas, NV (US); R. Jacob Baker, Las Vegas, NV (US)

(73) Assignee: The Board of Regents of the Nevada System of Higher Education on Behalf of the University of Nevada, Las Vegas, NV (US)

( * ) Notice: Subject to any disclaimer, the term of this patent is extended or adjusted under 35 U.S.C. 154(b) by 710 days.

(21) Appl. No.: 17/884,203

(22) Filed: Aug. 9, 2022

(65) Prior Publication Data

US 2023/0397882 A1 Dec. 14, 2023

Related U.S. Application Data

(60) Provisional application No. 63/352,114, filed on Jun. 14, 2022.

(51) Int. Cl.

| | |
|---|---|
| ***A61B 5/00*** | (2006.01) |
| ***A61F 13/08*** | (2006.01) |
| *A61B 5/01* | (2006.01) |
| *A61B 90/00* | (2016.01) |

(52) U.S. Cl.

CPC ............ *A61B 5/6804* (2013.01); *A61F 13/08* (2013.01); *A61B 5/01* (2013.01); *A61B 2090/065* (2016.02); *A61B 2562/029* (2013.01)

(58) Field of Classification Search

CPC ... A61B 5/6804; A61B 5/01; A61B 2090/065; A61B 2562/029; A61B 5/026; A61B 5/1073; A61B 5/14542; A61B 5/742; A61B 5/7475; A61B 2562/0247; A61B 2562/18; A61B 5/6805; A61B 5/6806; A61B 5/6807; A61F 13/08

See application file for complete search history.

(56) References Cited

U.S. PATENT DOCUMENTS

| | | | | |
|---|---|---|---|---|
| 10,596,365 | B2 | 3/2020 | Hyde et al. | |
| 10,736,805 | B2 | 8/2020 | Johnson et al. | |
| 2015/0297437 | A1 | 10/2015 | Neuenhahn et al. | |
| 2017/0003149 | A1* | 1/2017 | Berk | G01D 11/24 |
| 2017/0079868 | A1 | 3/2017 | Reid, Jr. et al. | |
| 2017/0100300 | A1 | 4/2017 | Rapp et al. | |
| 2018/0015475 | A1* | 1/2018 | Arlett | G01N 35/00029 |
| 2018/0092781 | A1 | 4/2018 | Pan et al. | |
| 2018/0220972 | A1* | 8/2018 | Jeong | A61B 5/7475 |
| 2019/0094088 | A1* | 3/2019 | Reif | A61B 5/6807 |
| 2019/0239769 | A1* | 8/2019 | Lee | A61B 5/282 |
| 2019/0336055 | A1* | 11/2019 | Shah | A61B 5/0015 |
| 2020/0014163 | A1* | 1/2020 | Kwon | H01R 12/714 |
| 2020/0127398 | A1* | 4/2020 | Burns | H01R 12/7082 |

(Continued)

*Primary Examiner* — May A Abouelela
(74) *Attorney, Agent, or Firm* — Ballard Spahr LLP

(57) ABSTRACT

Methods, systems, and apparatuses are described for determining and outputting pressure and force data associated with one or more locations of a fabric configured to be flexibly warn underneath a compression garment.

20 Claims, 8 Drawing Sheets

(56) References Cited

U.S. PATENT DOCUMENTS

| | | | | |
|---|---|---|---|---|
| 2020/0178860 | A1* | 6/2020 | Masciotti | A61B 5/14532 |
| 2020/0232762 | A1* | 7/2020 | Hamilton | F41A 9/62 |
| 2020/0305793 | A1* | 10/2020 | Al-Jadda | A61B 5/6823 |
| 2020/0405239 | A1* | 12/2020 | Trabish | A61B 5/0004 |
| 2021/0077304 | A1 | 3/2021 | Xu et al. | |
| 2021/0153748 | A1 | 5/2021 | Rapp et al. | |
| 2021/0348886 | A1* | 11/2021 | Havens | F41G 1/473 |
| 2022/0087608 | A1* | 3/2022 | Lazou | A61B 5/1107 |
| 2022/0175311 | A1* | 6/2022 | Kim | A61B 5/681 |
| 2023/0042347 | A1* | 2/2023 | Lynch | A61B 5/6831 |
| 2025/0025772 | A1* | 1/2025 | Kong | G06F 3/044 |

* cited by examiner

PRESSURE SENSING COMPRESSION GARMENT

CROSS REFERENCE TO RELATED PATENT APPLICATION

This application claims priority to U.S. Provisional Application No. 63/352,114, filed Jun. 14, 2022, which is herein incorporated by reference in its entirety.

BACKGROUND

Venous stasis disease effects as many as 20 million people in the United States alone every year. Of those 20 million people, around 2.5 million (1 out of every 8) people suffer from Venous Stasis Ulcers (VSUs). Venous stasis disease, also known as chronic venous insufficiency (CVI), is a condition that occurs when the venous wall and/or valves in the leg veins are not working effectively, making it difficult for blood to return to the heart from the legs. CVI causes blood to pool, or collect, in these veins (e.g., stasis), and thus, can lead to varicose veins. The ulcer itself is typically a red rash of irritated skin which eventually develops into a painful open wound. Some VSUs are treated with leg elevation and compression therapy, while surgery is necessary in severe cases. Although the methods for treating VSUs vary on a cases-by-case bases, compression therapy is the standard of care in the United States healthcare system. Compression therapy works because the compression of the fatty layer of skin on the patient's leg pushes the blood that has pooled up in artificial veins back into the deep venous system. Once blood is back into the deep venous system, it can more easily flow back to the heart. The area most affected by venous skin ulcers is the lower leg, from the top of the foot to the middle of the shin. However, the entire lower leg from below the knee to the foot is susceptible to VSUs.

The fastest healing times for VSUs are achieved when an increasing gradient of pressure is applied to the patient's leg, wherein the lowest pressure is applied to the knee and the highest pressure is applied to the patient's foot. The highest pressures, applied at the ankle and foot area, should decrease linearly as the pressure is applied up to the knee. The application of such a gradient could decrease the time required for ulcers to heal from up to six months down to as little as 60 days, while also assisting in the prevention of recurrence. Although this method of applying a linear pressure gradient works very well in promoting the best blood flow, applying a known amount of absolute pressure to the leg, or to any parts of the body, is a difficult task. Modern treatment consists of the application of passive wraps and compression sleeves to the patient's leg with no knowledge of exactly how much pressure is being applied to the leg. However, it has not been shown that the application of wrapped compression garments can obtain specific pressures with accuracy or precision, and none of the providers applying these compression garments can reliably adjust for specific situations. Unfortunately, applying these compression garments with too much pressure usually results in longer healing times because the high pressure does not allow blood to flow back to the heart as necessary. Knowledge of the pressure being applied to the leg is desired, if not, essential, to the effective treatment and prevention of VSUs.

SUMMARY

It is understood that both the following general description and the following detailed description are exemplary and explanatory only and are not restrictive.

In an embodiment, disclosed are methods and apparatuses comprising receiving, by a computing device from one or more sensors, sensor data, wherein the one or more sensors are affixed to one or more locations of at least one of a person or an object, determining, based on the sensor data, information associated with the one or more locations, and outputting the information associated with the one or more locations.

In an embodiment, disclosed are methods and apparatuses comprising receiving, by a server via a computing device, sensor data, determining, based on the sensor data, information associated with one or more locations of at least one of a person or an object, and outputting the information associated with the one or more locations.

In an embodiment, disclosed are sensors comprising a first circuit board, a second circuit board, a force sensing mechanism affixed to the first circuit board, a turret pin mechanism affixed to the second circuit board, and one or more pogo pins, wherein the one or more pogo pins are configured to be connected between the first circuit board and the second circuit board.

In an embodiment, disclosed are sensors further comprising wherein the first circuit board is configured into a circular structure, and wherein the second circuit board is configured into a circular structure.

In an embodiment, disclosed are sensors further comprising wherein the force sensing mechanism is affixed to a top surface of the first circuit board, wherein the turret pin mechanism is affixed to a center portion of the second circuit board, and wherein the one or more pogo pins are affixed to the top surface of the first circuit board and a bottom surface of the second circuit board.

In an embodiment, disclosed are sensors further comprising wherein the turret pin mechanism is configured to protrude a predetermined length above the top surface of the second circuit board and a predetermined length below the bottom surface of the second circuit board.

In an embodiment, disclosed are sensors further comprising wherein the one or more pogo pins are configured to lift the second circuit board such that the turret pin mechanism does not contact the force sensing mechanism when no pressure is applied to the sensor.

In an embodiment, disclosed are sensors further comprising wherein the one or more pogo pins comprise one or more low-profile spring-loaded brass pogo pins.

In an embodiment, disclosed are sensors further comprising wherein the one or more pogo pins are configured to be equidistantly spaced from each other around the first circuit board.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of the present description serve to explain the principles of the methods and systems described herein. To easily identify the discussion of any particular element or act, the most significant digit or digits in a reference number may refer to the figure number in which that element is first introduced.

DETAILED DESCRIPTION

Figure 1:
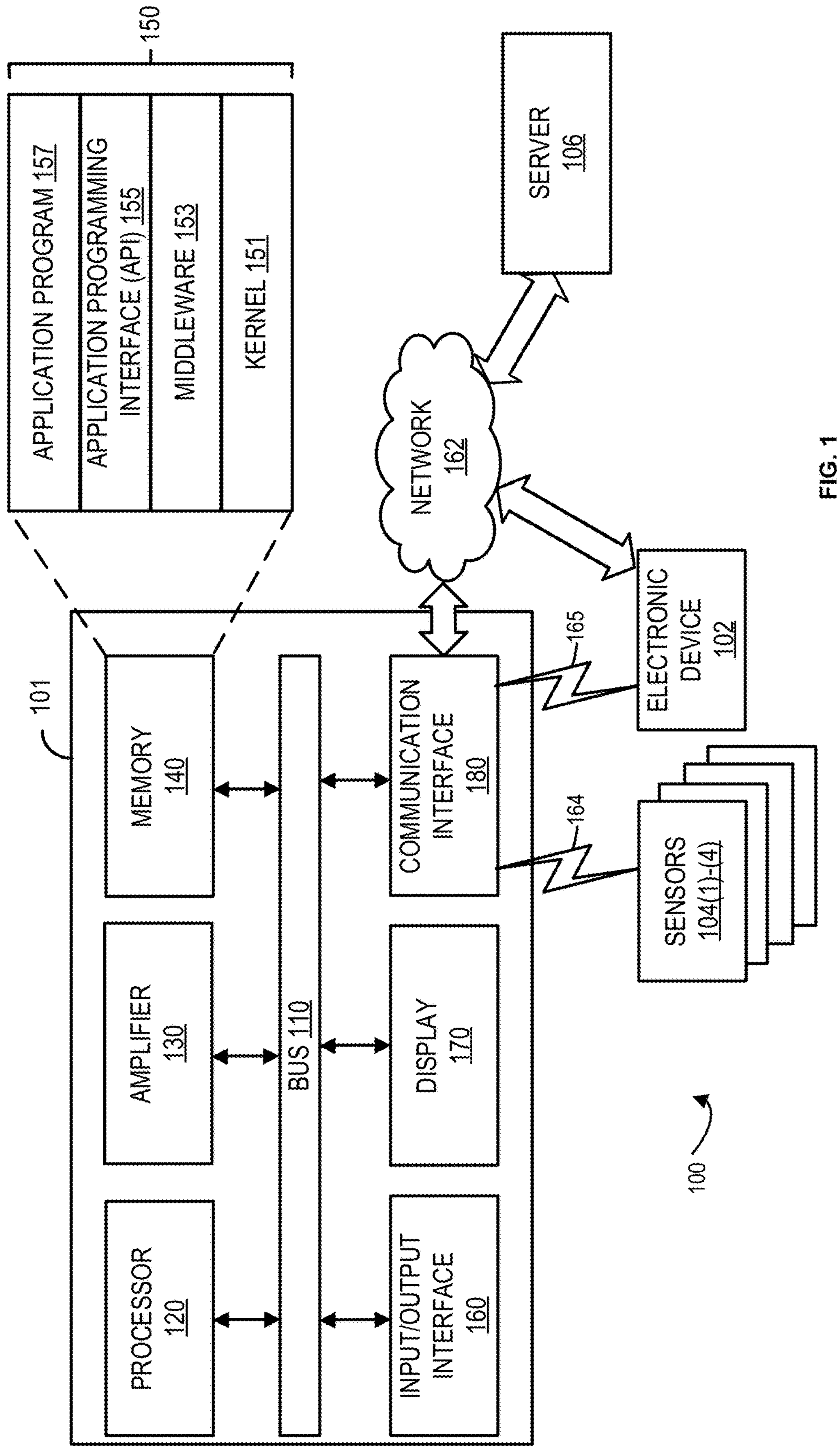
FIG. 1 shows an example network environment.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms “a,” “an” and “the” include plural referents unless the context clearly dictates otherwise. Ranges may be expressed herein as from “about” one particular value, and/or to “about” another particular value. When such a range is expressed, another embodiment includes—from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint.

“Optional” or “optionally” means that the subsequently described event or circumstance may or may not occur, and that the description includes instances where said event or circumstance occurs and instances where it does not.

Throughout the description and claims of this specification, the word “comprise” and variations of the word, such as “comprising” and “comprises,” means “including but not limited to,” and is not intended to exclude, for example, other components, integers or steps. “Exemplary” means “an example of” and is not intended to convey an indication of a preferred or ideal embodiment. “Such as” is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, a computer program product on a computer-readable storage medium (e.g., non-transitory) having processor-executable instructions (e.g., computer software) embodied in the storage medium. More particularly, the present methods and systems may take the form of web-implemented computer software. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These processor-executable instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These processor-executable instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The processor-executable instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Hereinafter, various embodiments of the present disclosure will be described with reference to the accompanying drawings. As used herein, the terms “user,” or “subject,” may indicate a person who uses an electronic device or a device (e.g., an artificial intelligence electronic device) that uses an electronic device.

“Functional fabric,” “fabric,” or “undergarment” refer to a substrate having an inner facing and outer facing surface, with the inner facing surface directed to a user’s skin and the outer facing surface away from the skin, with a material thickness separating the surfaces. The functional fabric, or fabric, may be a textile, undergarment, or garment. The functional fabric, or fabric, may be, for example, a medical wrap, bandage, medical garment, an inelastic functional fabric, an elastic functional fabric, a woven functional fabric, a non-woven functional fabric or a knit functional fabric. An undergarment may be any functional fabric, or fabric, configured to be flexibly worn underneath a garment. A garment may be a sock, stocking, sleeve, glove, shirt, tights, skull cap, or other type of clothing. A garment may also refer to wraps, bandages, wound dressings, braces, hard casts, soft casts, splints, pneumatic compression devices and other medical devices. A functional fabric, or fabric, as described herein may be an undergarment configured to be flexibly worn underneath a therapeutic compression stocking. The functional fabric, or fabric, may be moistened, heated or cooled, including a precise manner and/or feedback-type loop. A functional fabric, or fabric, may also refer to performance or smart garments, for example, performance athletic wear with additional smart properties such as cooling, heating, aiding recovery or reducing muscle soreness (e.g. reducing lactic acid), preventing injury, sweat wicking, adding moisture, compression, antibacterial properties, polymer coatings and the like. The functional fabric may have a diagnostic and/or monitoring function, such a monitoring or adjusting a physical or physiological parameter such as temperature, pressure, blood oxygen, UV exposure, limb volume, and the like. Accordingly, the term "functional" in a functional fabric refers to a fabric having one or more sensors to provide useful and actionable information, with that information specific for an application of interest. For example, confirmation of pressure, length of time worn, an environmental parameter such as heat, light intensity, moisture, a skin-specific property such as oxygenation, blood flow, skin discoloration or redness.

"Pressure sensor" refers to a device capable of generating a signal corresponding to a pressure generated between the undergarment and the tissue or skin of a wearer of the undergarment. Pressure sensors may include capacitive pressure sensors or piezoresistant (piezoelectric) sensors. In embodiments, pressure sensors have a thickness of less than or equal to 10 mm, less than or equal to 5 mm, less than or equal to 2.5 mm, or optionally, less than or equal to 1 mm. Pressure sensors, in some embodiments, may further measure circumferential leg pressure, for example, to estimate leg volume.

Each of the constitutional elements described in the present document may consist of one or more components, and names thereof may vary depending on a type of an electronic device. The electronic device according to various exemplary embodiments may include at least one of the constitutional elements described in the present document. Some of the constitutional elements may be omitted, or additional other constitutional elements may be further included. Further, some of the constitutional elements of the electronic device according to various exemplary embodiments may be combined and constructed as one entity, so as to equally perform functions of corresponding constitutional elements before combination.

Methods and systems are described for outputting pressure data. A computing device may receive sensor data from one or more sensors affixed to one or more locations of at least one of a person or an object based on an event such as a user input or a predetermined time interval. The object may comprise at least one of a fabric, an undergarment, a wheelchair, or a hospital bed. The computing device may comprise at least one of a smartphone, a laptop, a desktop, or a tablet. The sensor data may comprise voltage data, or current data, associated with a pressure applied at the one or more locations. In an embodiment, the one or more sensors may be embedded into one or more locations of the object. In an embodiment, the one or more sensors may comprise at least one of a temperature sensor or a humidity sensor. The one or more locations may be associated with predetermined areas of a person's leg, such as an upper calf, a lower calf, a lower leg, or an insole of the foot. The undergarment, or fabric, may be configured to be flexibly worn over an extremity of a user and to be positioned underneath an adjustable garment, wherein the adjustable garment may comprise a compression garment. The computing device may process the sensor data to determine force data associated with the one or more locations. The computing device may process the force data to determine pressure data associated with the one or more locations. The computing device may transmit the force data and the pressure data to an electronic device, such as a smartphone, to be output to a user. In an embodiment, the computing device may output the force data and the pressure data to a communication network for remote access by other electronic devices. In an embodiment, the computing device may output the sensor data to a server, wherein the server may perform the functions of processing the sensor data and outputting the force data and the pressure data to an electronic device. In an embodiment, the sensors may be encapsulated to protect the sensors from water, perspiration or external environmental hazards such as humidity, heat, cold, and the like.

In an embodiment, sensor devices are described for outputting the sensor data. The sensor devices may comprise a force sensing mechanism enclosed in a housing unit. The housing unit may comprise one or more pogo pins connected between a first printed circuit board (PCB) and a second PCB. The force sensing mechanism may be affixed to a top surface of the first PCB. The second PCB may contain a turret pint mechanism that may be affixed to a center portion of the second PCB, with a predetermined length protruding from the top surface of the second PCB and a predetermined length protruding from the bottom surface of the second PCB. The one more pogo pins may be affixed to a top surface of the first PCB and a bottom surface of the second PCB. The one or more pogo pins may be configured to be equidistantly spaced around the PCB. For example, if using four pogo pins, the pogo pins may be evenly spaced 90 degrees around the PCB. The one or more pogo pins may be configured to lift the second circuit board such that the turret pin mechanism does not contact the force sensing mechanism when no pressure is applied to the sensor device. The one or more pogo pins may comprise one or more low-profile spring-loaded brass pogo pins. Each printed circuit board may be configured into a circular structure.

In an embodiment, the sensor devices may further comprise an amplifier in communication with the force sensing mechanism. The amplifier may be affixed to either the first PCB or to the computing device. The amplifier may be configured to amplify the voltage data received from the sensor devices and output the amplified voltage data to the computing device.

FIG. 1 shows an exemplary network environment including an electronic device (e.g., smartphone or laptop) configured for controlling one or more guidance systems of one or more other electronic devices (e.g., a headset device or sensor device) according to various embodiments. Referring to FIG. 1, a computing device 101 in a network environment 100 is disclosed according to various exemplary embodiments. The computing device 101 may include a bus 110, a processor 120, an amplifier 130, a memory 140, an input/output interface 160, a display 170, and a communication interface 180. In a certain exemplary embodiment, the computing device 101 may omit at least one of the aforementioned constitutional elements or may additionally include other constitutional elements. The computing device 101 may comprise a microcontroller, or a printed circuit board. In an embodiment, the computing device 101 may be, for example, a mobile phone, a smart phone, a tablet computer, a laptop, a desktop computer, a smartwatch, and the like.

The computing device 101 may be affixed to an undergarment, or a fabric, that may be configured to be flexibly worn over a person's limb, wherein the undergarment, or the fabric, may be further configured to be positioned underneath an adjustable garment, such as a compression garment. The computing device 101 may be configured to process the output voltage signals received from the sensor devices 104(1)-(4). In an embodiment, the computing device 101 may forward the received output voltage signals to an external electronic device 102 for further processing. In an embodiment, the computing device 101 may forward the received output voltage signals to a server 106 for further processing, wherein the server 106 may process the received output voltage signal and transmit the processed data to the electronic device 102.

The bus 110 may include a circuit for connecting the aforementioned constitutional elements 110 to 180 to each other and for delivering communication (e.g., a control message and/or data) between the aforementioned constitutional elements. For instance, the bus 110 may be designed to send the sensor data from the processor 120 to the communication interface 180 in order to further transmit the sensor data to an external device such as the electronic device 102 or a server 106.

The processor 120 may include one or more of a Microcontroller Unit (MCU), a Central Processing Unit (CPU), an Application Processor (AP), and a Communication Processor (CP). The processor 120 may control, for example, at least one of the other constitutional elements of the computing device 101 and/or may execute an arithmetic operation or data processing for communication. The processing (or controlling) operation of the processor 120 according to various embodiments is described in detail with reference to the following drawings. The processor 120 may include an on-chip analog-to-digital converter (ADC) for converting the amplified voltage signal, received from the amplifier 130 (described below), from an analog signal to a digital signal. The processor 120 may be used to process the digital signal in order to calculate the force applied to each sensor location in Newtons, and the associated pressure in mmHg. The processor 120 may then send the processed data, including the force data and pressure data, to the communication interface 180 (which may include a Bluetooth module as shown below) using a Universal Asynchronous Receiver/Transmitter (UART), wherein the communication interface 180 may further transmit the force data and the pressure data to an external electronic device 102, such as a smart phone, or a server 106.

The amplifier 130 may include an instrumentation amplifier such as a MAX4208. A separate amplifier 130 may be used for each sensor device 104(1)-(4) in order to amplify the output voltage signal received from each sensor. In an embodiment, each amplifier 130 may be included on the sensor device 104(1)-(4) instead of the computing device 101. Since the output voltage signal from the sensor devices 104(1)-(4) is very small relative to the supply voltage, the output voltage signal is amplified using the amplifier 130 in order to obtain optimal results from the ADC.

The memory 140 may include a volatile and/or non-volatile memory. The memory 140 may store, for example, a command or data related to at least one different constitutional element of the computing device 101. According to various exemplary embodiments, the memory 140 may store a software and/or a program 150. The program 150 may include, for example, a kernel 151, a middleware 153, an Application Programming Interface (API) 155, and/or an application program (or an "application") 157, or the like, configured for controlling one or more functions of the computing device 101 and/or an external device. At least one part of the kernel 151, middleware 153, or API 155 may be referred to as an Operating System (OS). The memory 140 may include a computer-readable recording medium having a program recorded therein to perform the method according to various embodiments by the processor 120.

The kernel 151 may control or manage, for example, system resources (e.g., the bus 110, the processor 120, the memory 130, etc.) used to execute an operation or function implemented in other programs (e.g., the middleware 153, the API 155, or the application program 157). Further, the kernel 151 may provide an interface capable of controlling or managing the system resources by accessing individual constitutional elements of the computing device 101 in the middleware 153, the API 155, or the application program 157.

The middleware 153 may perform, for example, a mediation role so that the API 155 or the application program 157 can communicate with the kernel 151 to exchange data.

Further, the middleware 153 may handle one or more task requests received from the application program 157 according to a priority. For example, the middleware 153 may assign a priority of using the system resources (e.g., the bus 110, the processor 120, or the memory 140) of the computing device 101 to at least one of the application programs 157. For instance, the middleware 153 may process the one or more task requests according to the priority assigned to the at least one of the application programs, and thus may perform scheduling or load balancing on the one or more task requests.

The API 155 may include at least one interface or function (e.g., instruction), for example, for file control, window control, video processing, or character control, as an interface capable of controlling a function provided by the application program 157 in the kernel 151 or the middleware 153.

For example, the input/output interface 160 may play a role of an interface for delivering an instruction or data input from a user or a different external device(s) to the different constitutional elements of the computing device 101. Further, the input/output interface 160 may output an instruction or data received from the different constitutional element(s) of the computing device 101 to the different external device.

The display 170 may include various types of displays, for example, a Liquid Crystal Display (LCD) display, a Light Emitting Diode (LED) display, an Organic Light-Emitting Diode (OLED) display, a MicroElectroMechanical Systems (MEMS) display, or an electronic paper display. The display 170 may display, for example, a variety of contents (e.g., text, image, video, icon, symbol, etc.) to the user. The display 170 may include a touch screen. For example, the display 170 may receive a touch, gesture, proximity, or hovering input by using a stylus pen or a part of a user's body.

The communication interface 180 may establish, for example, communication between the computing device 101 and an external device (e.g. an electronic device 102, one or more sensor devices 104(1)-(4), or a server 106). In one example, the communication interface 180 may communicate with the external device (e.g., the server 106) by being connected to a network 162 through wireless communication or wired communication.

In another example, as a cellular communication protocol, the wireless communication may use at least one of Long-Term Evolution (LTE), LTE Advance (LTE-A), Code Division Multiple Access (CDMA), Wideband CDMA (WCDMA), Universal Mobile Telecommunications System (UMTS), Wireless Broadband (WiBro), Global System for Mobile Communications (GSM), and the like. Further, the wireless communication may include, for example, a near-distance communication 164, 165. The near-distance communications 164, 165 may include, for example, at least one of Bluetooth, Wireless Fidelity (WiFi), Near Field Communication (NFC), Global Navigation Satellite System (GNSS), and the like. According to a usage region or a bandwidth or the like, the GNSS may include, for example, at least one of Global Positioning System (GPS), Global Navigation Satellite System (Glonass), Beidou Navigation Satellite System (hereinafter, "Beidou"), Galileo, the European global satellite-based navigation system, and the like. Hereinafter, the "GPS" and the "GNSS" may be used interchangeably in the present document. The wired communication may include, for example, at least one of Universal Serial Bus (USB), High Definition Multimedia Interface (HDMI), Recommended Standard-232 (RS-232), power-line communication, Plain Old Telephone Service (POTS), and the like. The network 162 may include, for example, at least one of a telecommunications network, a computer network (e.g., LAN or WAN), the internet, and a telephone network.

In an embodiment, the computing device 101 may forward the output voltage signals, received from the sensor devices 104(1)-(4), to a server 106 for processing via network 162. The server 106 may perform the processing steps, performed by the computing device 101, for processing the output voltage signals in order to calculate the force applied to each sensor location in Newtons, and the associated pressure in mmHg. The server 106 may then transmit the processed data to the electronic device 102 via the network 162.

The electronic device 102 may comprise a mobile phone, a smart phone, a tablet computer, a laptop, a desktop computer, a smartwatch, and the like. The electronic device 102 may receive the sensor data of the one or more sensors devices 104(1)-(4) from the computing device 101 via the communication interface 180. The electronic device 102 may then output the received sensor data to the user. In an embodiment, the electronic device 102 may receive the sensor data from the server 106 via network 162. For example, the server 106 may receive the amplified output voltage signals from the computing device 101 and process the signals to calculate the force applied to each sensor location in Newtons, and the associated pressure in mmHg. The server 106 may then transmit the sensor data to the electronic device 102 to be output to the user. In an embodiment, the computing device 101 may transmit the digital signals of the amplified output voltage signals to the electronic device 102 for processing. For example, the electronic device 102 may process the digital signal in order to calculate the force applied to each sensor location in Newtons, and the associated pressure in mmHg. In an embodiment, the electronic device 102 may include a smartphone application for interfacing with the sensor data and displaying the sensor data to the user.

Figure 2A:
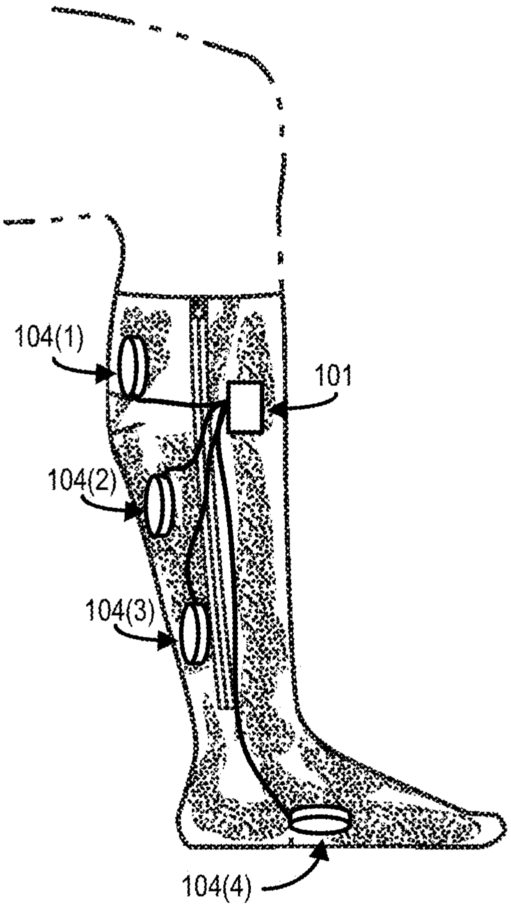
FIGS. 2A and 2B show example sensor configurations.
Figure 2B:
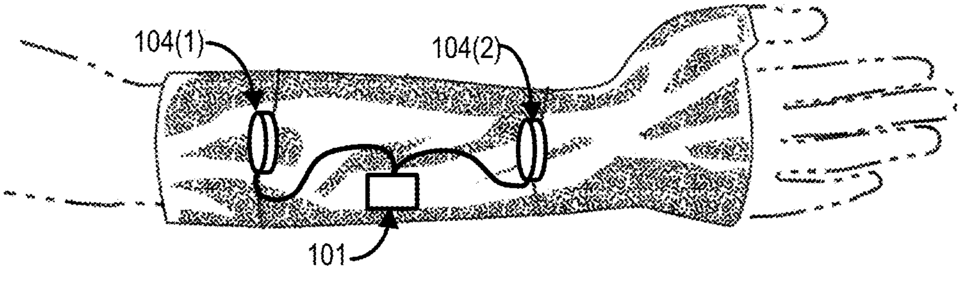

The sensor devices 104(1)-(4) may comprise one or more force sensor devices such as the 303A and 003A sensors. The sensor devices 104(1)-(4) are configured to provide an output voltage signal based on the pressure applied to the sensor. In an embodiment, the sensor devices 104(1)-(4) may provide an output current signal based on the pressure applied to the sensor. The most efficient method of correctly determining absolute pressure is to first measure force, calculated from the output voltage signal, and then calculate pressure from the force data and a predetermined area. As described in further detail below, each sensor device 104(1)-(4) may be enclosed in a housing mechanism comprising a top printed circuit board (PCB) and a bottom PCB, wherein the top PCB and the bottom PCB may be connected to each other by several low-profile brass pogo pins in order to form a spring-loaded housing mechanism for each force sensor device 104(1)-(4). The sensor devices 104(1)-(4) may be affixed to a top surface of the bottom PCB. In an embodiment, an amplifier 103 may be affixed to the top surface of each bottom PCB instead of the computing device 101. The housing mechanism of the sensors devices 104(1)-(4) may be affixed to several locations on the same undergarment to which the computing device 101 is affixed, as shown in FIGS. 2A and 2B. The undergarment may be configured to be flexibly worn over a person's limb and underneath a compression garment. In an embodiment, the undergarment may be worn on the lower leg, wherein the sensors may be located on the upper calf, the lower calf, the lower leg, and the insole of the foot, as shown in FIGS. 2A and 2B. Each sensor device 104(1)-(4) may be used to monitor the pressure applied to its location on the undergarment, and thus, the pressure applied to its location on the user. In an embodiment, the sensor devices 104(1)-(4) may be embedded into the undergarment. In an embodiment, the sensor devices 104(1)-(4) may be affixed directly on a person's limb. For example, the sensor devices 104(1)-(4) may be worn directly under a compression garment, in contact with the person's skin, in order to determine the pressure applied to each sensor location. In an embodiment, the sensor devices 104(1)-(4) may be affixed to a wheelchair or a hospital bed. For example, the sensor devices 104(1)-(4) may be affixed to a hospital bed in order to determine whether a person, that has been bed ridden, needs to be shifted. For example, it may be determined that the person's position needs to be shifted after determining that the person has experienced a predetermined pressure for a predetermined period of time for a particular position. The sensor data received from sensor devices 104(1)-(4) may be used to determine a pressure gradient of pressure being applied to a person's limb, such as the person's leg or arm. The sensor devices 104(1)-(4) may transmit the output voltage signals to the amplifiers 103, wherein the amplified output voltage signals may then be transmitted to the computing device 101 for further processing. In an embodiment, the sensor devices 104(1)-(4) may be encapsulated to protect the sensors from water, perspiration or external environmental hazards such as humidity, heat, cold, and the like. In an embodiment, the sensor devices 104(1)-(4) may comprise at least one of a temperature sensor or a humidity sensor.

According to one exemplary embodiment, the server 106 may include a group of one or more servers. According to various exemplary embodiments, all or some of the operations executed by the computing device 101 may be executed in a different one or a plurality of electronic devices (e.g., the electronic device 102 or the server 106). For example, the processing of the output voltage signals received from the sensor devices 104(1)-(4) may be performed by either the electronic device 102 or the server 106. According to one exemplary embodiment, if the computing device 101 needs to perform a certain function or service either automatically or based on a request, the computing device 101 may request at least some parts of functions related thereto alternatively or additionally to a different electronic device (e.g., the electronic device 102 or the server 106) instead of executing the function or the service autonomously. The different electronic devices (e.g., the electronic device 102 or the server 106) may execute the requested function or additional function, and may deliver a result thereof to the computing device 101 or to the electronic device 102. The computing device 101 may provide the requested function or service either directly or by additionally processing the received result. For this, for example, a cloud computing, distributed computing, or client-server computing technique may be used.

FIGS. 2A and 2B show exemplary sensor configurations. The sensor configurations may comprise various components which may be in communication with some or other or all components. In FIGS. 2A and 2B, the computing device 101 is in communication with the sensor devices 104(1)-(4), wherein the devices are affixed to an undergarment worn over a person's limb. In an embodiment, the sensor devices 104(1)-(4) may be embedded into one or more locations of the undergarment. In an embodiment, the sensor configuration may include additional sensors, such as a temperature sensor and/or a humidity sensor, in communication with the computing device 101, wherein the additional sensors may also be affixed to the undergarment. FIG. 2A shows an exemplary sensor configuration wherein the computing device 101 and sensor devices 104(1)-(4) are affixed to an undergarment worn over a person's lower leg and foot. Sensor device 104(1) is affixed to an upper calf location, sensor device 104(2) is affixed to a lower calf location, sensor device 104(3) is affixed to a lower leg location, and sensor device 104(4) is affixed to a location of the insole of the foot. FIG. 2B shows an exemplary sensor configuration wherein the computing device 101 and sensor devices 104(1)-(2) are affixed to an undergarment worn over a person's forearm. Sensor device 104(1) is affixed to a location near the elbow while sensor device 104(2) is affixed to a location near the wrist. In an embodiment, the sensor devices 104(1)-(4) may be configured to each individually wirelessly connect to the electronic device 102 instead of using a computing device 101 affixed to the undergarment, wherein the sensor devices 104(1)-(4) may directly transmit the output voltage signals, or amplified output voltage signals, to the electronic device 102 for further processing. In an embodiment, the sensor devices 104(1)-(4) may be affixed directly on to the person's skin instead of to an undergarment.

Figure 3:
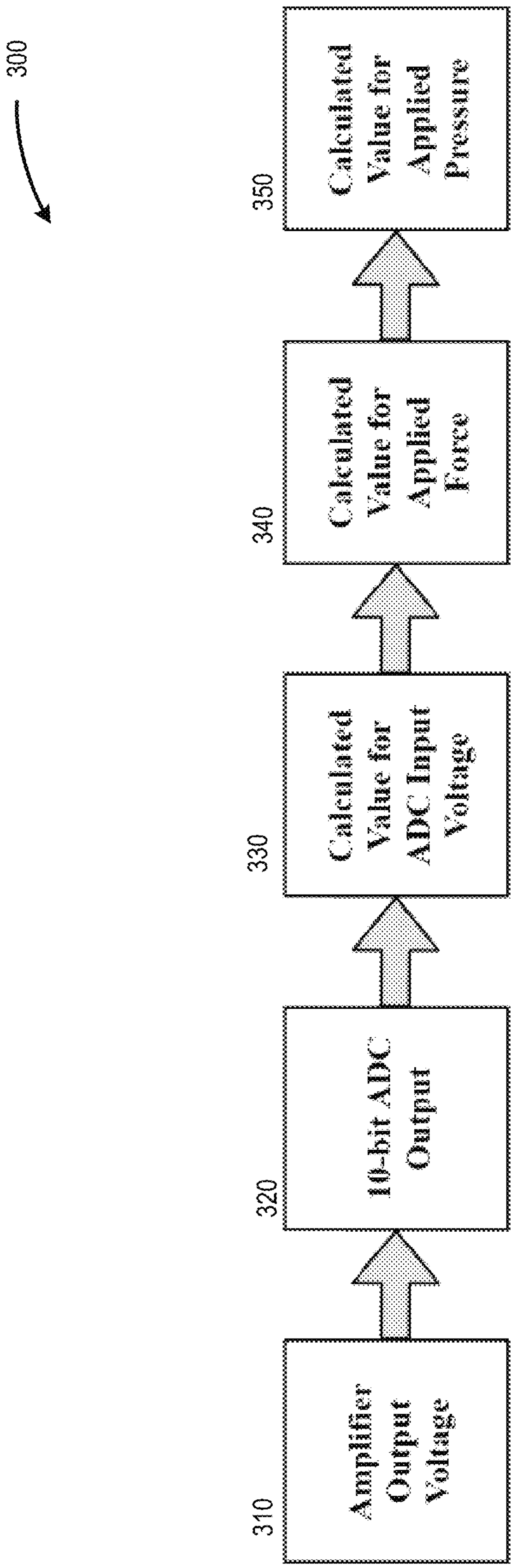
FIG. 3 shows an example data processing method.

FIG. 3 show an exemplary data processing method 300. Obtaining a pressure reading from the force applied to force sensor devices 104(1)-(4) requires a sequence of data processing steps. The steps may be implemented in whole or in part, by one or more of, the computing device 101, the electronic device 102, or the server 106, or any other suitable device. At step 310, the force sensor's output voltage signal is received and amplified by an amplifier. Once the signal is amplified, the signal is sent to an analog-to-digital converter (ADC). At step 320, the ADC converts the analog voltage signal into a digital value between 0 and 1023, wherein 0 corresponds to 0V and 1023 corresponds to a voltage of 1 least significant bit (LSB) less than the supply voltage. The corresponding voltage for the digital output value may be obtained by multiplying the digital output value by the LSB voltage. At step 330, the voltage corresponding to the ADC output is calculated. At step 340, the force may be calculated based on the calculated voltage. The force may be calculated using the sensitivity value of the force sensor. At step 350, the applied pressure value is obtained based on the calculated force value. The corresponding applied pressure values may be obtained by dividing the force by a predetermined area, such as the area over which the force is being applied. In the case of the sensor devices 104(1)-(4), the area may be calculated using the area of the housing mechanism of the sensor devices 104(1)-(4). The pressure applied to a sensor location of the undergarment may be calculated by dividing the area of the housing mechanism by an applied force.

Figure 4:
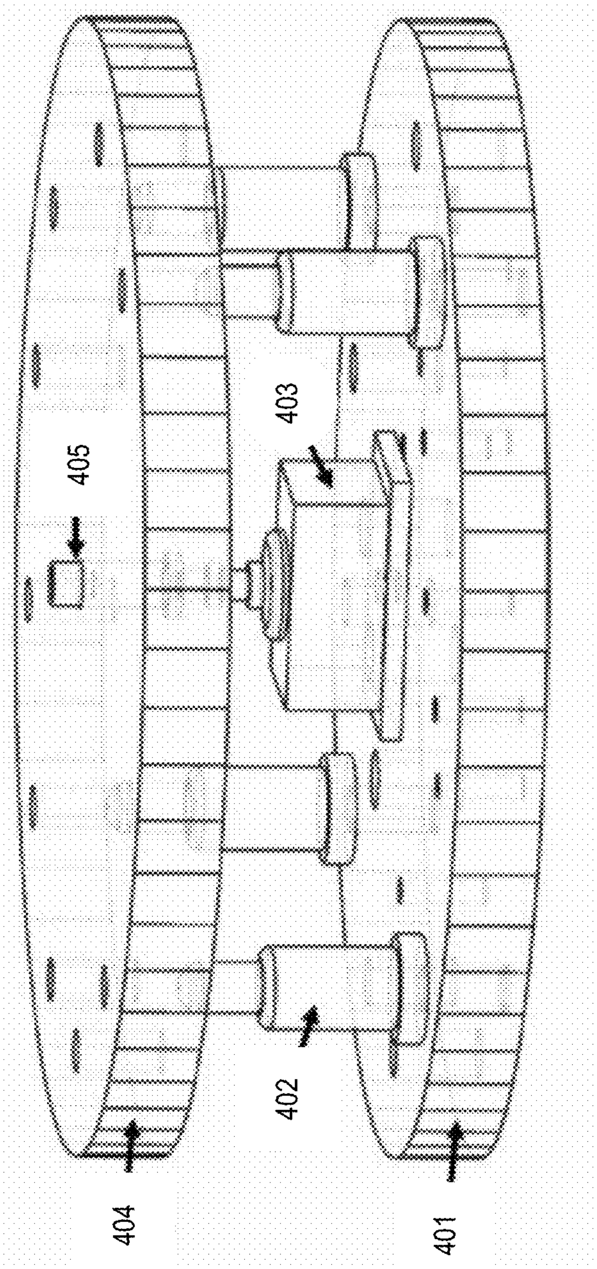
FIG. 4 shows an example sensor device housing mechanism.

FIG. 4 shows an exemplary sensor device housing mechanism (e.g., sensor device housing unit). The sensor device housing mechanism may include two printed circuit boards (PCBs), 401 and 404, connected to each other through the use of low-profile brass pogo pins 402, wherein the sensor device 403 may be housed between the two PCBs, 401 and 404. The first PCB 401 may comprise the bottom PCB, wherein the sensor device 403 may be affixed to a top surface of the first PCB 401. In an embodiment, the first PCB 401 may also include the amplifier 130, communicatively coupled to the sensor device 403 and affixed to a top surface of the first PCB 401. The second PCB 404 may comprise the top PCB and may comprise a PCB containing no electronic components. The second PCB 404 may comprise identical dimensions of the first PCB 401. The pogo pins 402 may be equidistantly spaced around the PCB. For example, if using four pogo pins 402, as depicted in FIG. 4, the pogo pins may be evenly spaced 90 degrees around the circular PCB. The housing mechanism provides the force sensor device 403 with protection from damage and an assurance that the sensor device 403 senses the correctly applied force. Specifically, the housing mechanism provides the force sensor with protection form damaging forces applied at any angle greater than 5 degrees by limiting the forces applied to the sensor to only be applied to the turret pin 405. The mechanics of the housing mechanism ensure that the sensor does not read pressure before the compression wrap is applied to the limb. For example, the spring force of the pogo pins provides enough force to keep the top PCB lifted when there is no pressure being applied to the sensor location, such that the turret pin 405 does not contact the sensor device 403.

Figure 5A:
FIGS. 5A and 5B show an example software application interface.
Figure 5B:
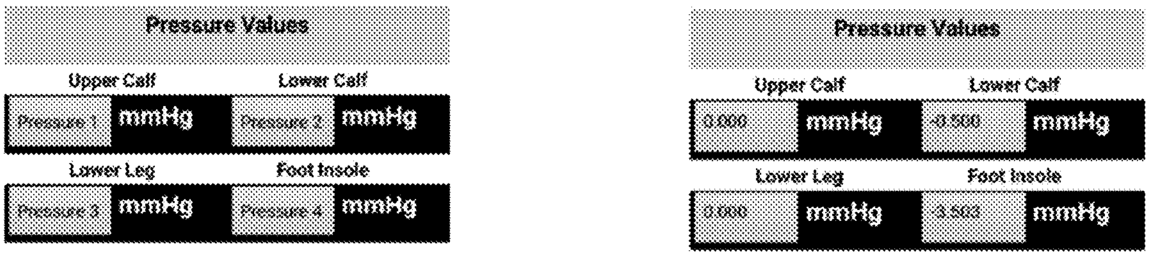

FIGS. 5A and 5B show an exemplary application interface, designed to be implemented using the electronic device 102, such as a smartphone. The smartphone application may be designed using the web-based MIT App Inventor and may be compatible with Android and Apple devices. In FIG. 5A, the first (left) screen may contain the home screen (Screen 1), which may be the default screen when the application is first opened. The second (right) screen may contain the "Technician" screen (Screen 2), which is only meant to be accessed by the nurse or technician who is working with the patient who owns the device. In FIG. 5B, the application may display the pressure values for each sensor, as well as the force and voltage values, along with a few metrics for viewing the battery life. In an embodiment, the application may display additional sensor values, such as temperature values and/or humidity values.

Figure 6:
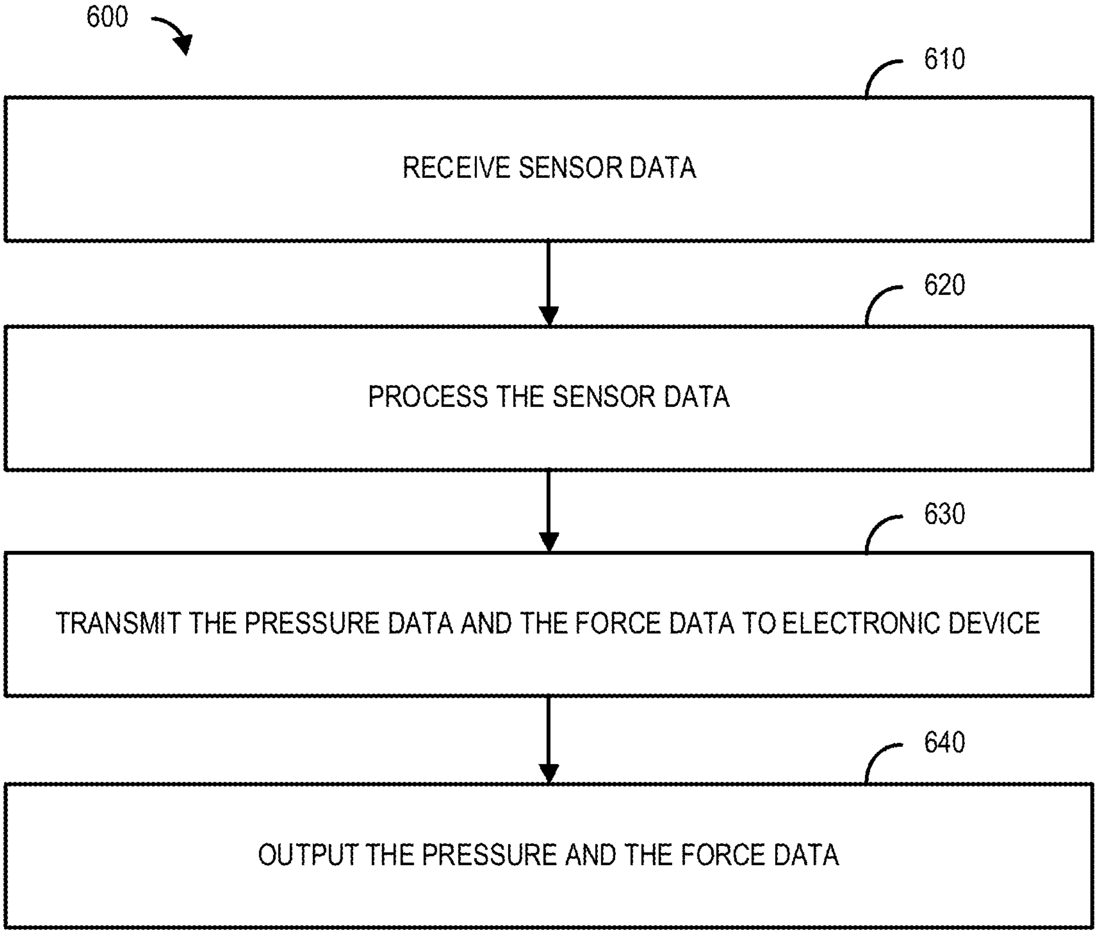
FIG. 6 shows an example method.

FIG. 6 shows an exemplary method 600 of determining the pressure applied to the locations of the sensor devices 104(1)-(4). The method may be implemented by the computing device 101, the electronic device 102, the server 106, or any combination thereof. At step 610, the sensor data is received from the sensor devices 104(1)-(4). For example, the sensor devices 104(1)-(4) may transmit the sensor data to the computing device 101 via a Bluetooth connection 164.

In an embodiment, the sensor data may be received from the sensors devices 104(1)-(4) based on a trigger event, such as a user input or a predetermined time interval. The sensor data may comprise output voltage signals, or output current signals, generated by the sensor devices 104(1)-(4) based on the pressure applied to the locations of the sensors. The output voltage signals received from the sensor devices 104(1)-(4) may be sent to an amplifier in order to amplify the output voltage signals, and thus, obtain optimal results from the analog-to-digital converter (ADC). At step 620, the amplified output voltage signals may be processed in order to determine the force values, or data, associated with the pressure applied to the locations of the sensor devices 104(1)-(4). The force values may be further processed in order to determine the pressure values, or data, associated with the pressure applied to the sensor locations. At step 630, the pressure values and the force values may be transmitted to an electronic device, such as a smartphone. For example, the computing device 101 may transmit the pressure values and the force values to the electronic device 102 via a Bluetooth connection 165. At step 640, the electronic device may output the pressure values and the force values for display to the user. For example, the electronic device 102, such as a smartphone, may utilize a smartphone application, like the application shown in FIGS. 5A and 5B, to display the pressure values and the force values.

Figure 7:
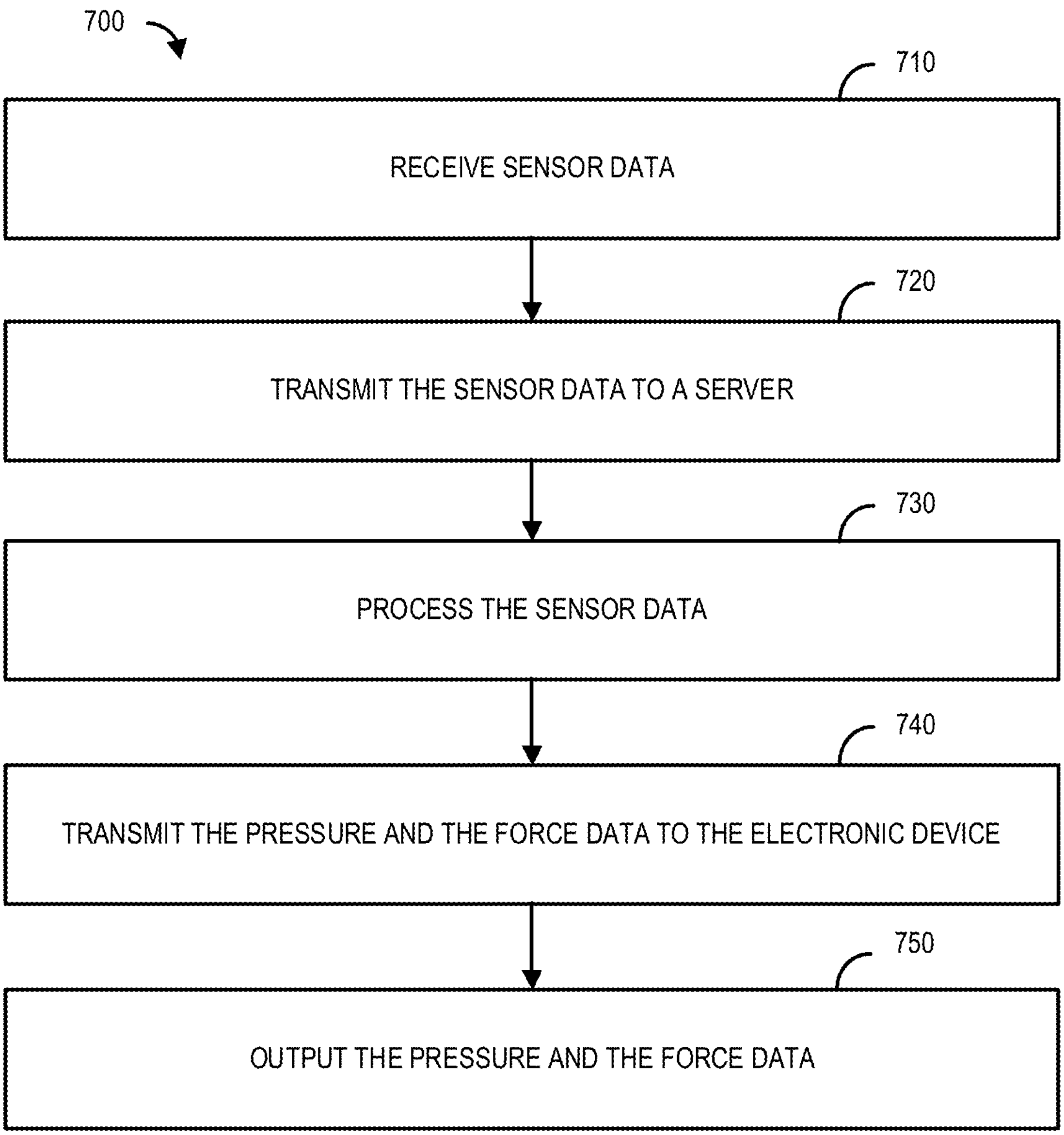
FIG. 7 shows an example method.

FIG. 7 shows an exemplary method 700 of determining the pressure applied to the locations of the sensor devices 104(1)-(4). The method may be implemented by the computing device 101, the electronic device 102, the server 106, or any combination thereof. At step 710, the sensor data is received from the sensor devices 104(1)-(4). For example, the sensor devices 104(1)-(4) may transmit the sensor data to the computing device 101 via a Bluetooth connection 164. In an embodiment, the sensor data may be received from the sensors devices 104(1)-(4) based on a trigger event, such as a user input or a predetermined time interval. The sensor data may comprise output voltage signals, or output current signals, generated by the sensor devices 104(1)-(4) based on the pressure applied to the locations of the sensors. The output voltage signals received from the sensor devices 104(1)-(4) may be sent to an amplifier in order to amplify the output voltage signals, and thus, obtain optimal results from the analog-to-digital converter (ADC). At step 720, the amplified output voltage signals may be sent to a server, such as the server 106 via network 162, for further processing. At step 730, the amplified output voltage signals may be processed in order to determine the force values, or data, associated with the pressure applied to the locations of the sensor devices. The force values may be further processed in order to determine the pressure values, or data, associated with the pressure applied to the sensor locations. At step 740, the pressure values and the force values may be transmitted from the server to an electronic device, such as a smartphone. For example, the server 106 may transmit the pressure values and the force values to the electronic device 102 via network 162. At step 750, the electronic device may output the pressure values and the force values for display to the user. For example, the electronic device 102, such as a smartphone, may utilize a smartphone application, like the application shown in FIGS. 5A and 5B, to display the pressure values and the force values to the user.

Figure 8:
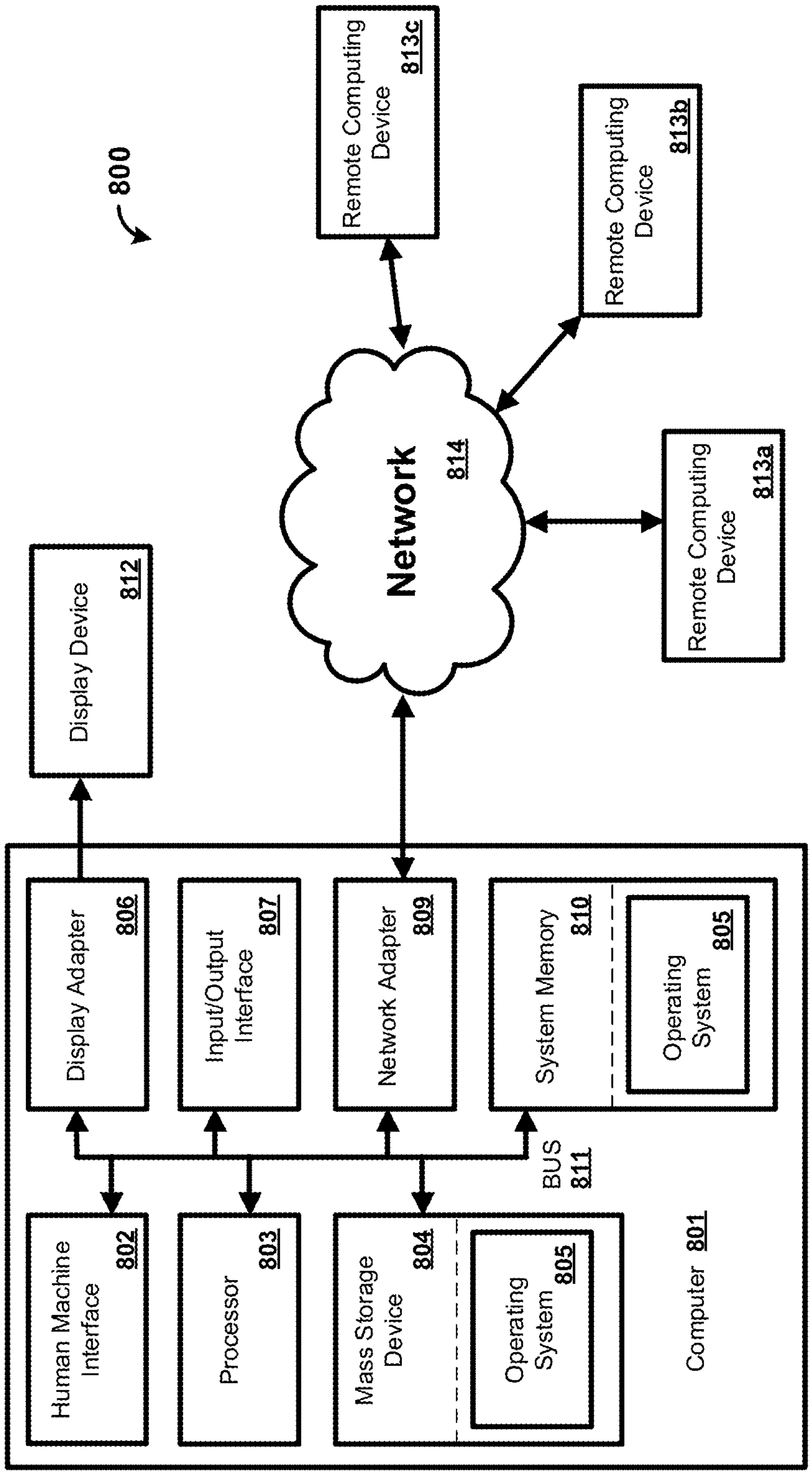
FIG. 8 shows an example computer.

In an exemplary aspect, the methods and systems can be implemented on a computer 801 as illustrated in FIG. 8 and described below. By way of example, the electronic device 102 of FIG. 1 can be a computer 801 as illustrated in FIG. 8. Similarly, the methods and systems disclosed can utilize one or more computers to perform one or more functions in one or more locations. FIG. 8 is a block diagram illustrating an exemplary operating environment 800 for performing the disclosed methods. This exemplary operating environment 800 is only an example of an operating environment and is not intended to suggest any limitation as to the scope of use or functionality of operating environment architecture. Neither should the operating environment 800 be interpreted as having any dependency or requirement relating to any one or combination of components illustrated in the exemplary operating environment 800.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, and/or the like that perform particular tasks or implement particular abstract data types. The disclosed methods can also be practiced in grid-based and distributed computing environments where tasks are performed by remote processing devices that are linked through a communications network. In a distributed computing environment, program modules can be located in local and/or remote computer storage media such as memory storage devices.

Further, one skilled in the art will appreciate that the systems and methods disclosed herein can be implemented via a general-purpose computing device in the form of a computer 801. The computer 801 can comprise one or more components, such as one or more processors 803, a system memory 810, and a bus 811 that couples various components of the computer 801 comprising the one or more processors 803 to the system memory 810. The system can utilize parallel computing.

The bus 811 can comprise one or more of several possible types of bus structures, such as a memory bus, memory controller, a peripheral bus, an accelerated graphics port, or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 811, and all buses specified in this description can also be implemented over a wired or wireless network connection and one or more of the components of the computer 801, such as the one or more processors 803, a mass storage device 804, an operating system 805, a network adapter 809, the system memory 810, an Input/Output Interface 807, a display adapter 806, a display device 812, and a human machine interface 802, can be contained within one or more remote computing devices 813*a,b,c* at physically separate locations, connected through buses of this form, in effect implementing a fully distributed system.

The computer 801 typically comprises a variety of computer readable media. Exemplary readable media can be any available media that is accessible by the computer 901 and comprises, for example and not meant to be limiting, both volatile and non-volatile media, removable and non-removable media. The system memory 810 can comprise computer readable media in the form of volatile memory, such as random access memory (RAM), and/or non-volatile memory, such as read only memory (ROM). The system memory 810 typically can comprise data such as the operating system 805 that is accessible to and/or is operated on by the one or more processors 803.

In an embodiment, the computer 801 can also comprise other removable/non-removable, volatile/non-volatile computer storage media. The mass storage device 804 can provide non-volatile storage of computer code, computer readable instructions, data structures, program modules, and other data for the computer 801. For example, the mass storage device 804 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 804, such as, by way of example, the operating system 805. The operating system 805 can comprise elements of the programming and be stored on the mass storage device 804. Examples of such databases comprise, DB2®, Microsoft® Access, Microsoft® SQL Server, Oracle®, mySQL, PostgreSQL, and the like. The databases can be centralized or distributed across multiple locations within the network 814.

In an embodiment, the user can enter commands and information into the computer 801 via an input device (not shown). Examples of such input devices comprise, but are not limited to, a keyboard, pointing device (e.g., a computer mouse, remote control), a microphone, a joystick, a scanner, tactile input devices such as gloves, and other body coverings, motion sensor, and the like These and other input devices can be connected to the one or more processors 803 via the human machine interface 802 that is coupled to the bus 811, but can be connected by other interface and bus structures, such as a parallel port, game port, an IEEE 1394 Port (also known as a Firewire port), a serial port, a network adapter 809, and/or a universal serial bus (USB).

In an embodiment, the display device 812 can also be connected to the bus 811 via an interface, such as the display adapter 806. It is contemplated that the computer 801 can have more than one display adapter 806 and the computer 801 can have more than one display device 812. For example, the display device 812 can be a monitor, an LCD (Liquid Crystal Display), light emitting diode (LED) display, television, smart lens, smart glass, and/or a projector. In addition to the display device 812, other output peripheral devices can comprise components such as speakers (not shown) and a printer (not shown) which can be connected to the computer 801 via an Input/Output Interface 807. Any step and/or result of the methods can be output in any form to an output device. Such output can be any form of visual representation, comprising, but not limited to, textual, graphical, animation, audio, tactile, and the like. The display device 812 and the computer 801 can be part of one device, or separate devices.

The computer 801 can operate in a networked environment using logical connections to one or more remote computing devices 813*a,b,c*. By way of example, a remote computing device 813*a,b,c* can be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computer 801 and a remote computing device 813*a,b,c* can be made via a network 814, such as a local area network (LAN) and/or a general wide area network (WAN). Such network connections can be through the network adapter 809. The network adapter 809 can be implemented in both wired and wireless environments. Such networking environments are conventional and commonplace in dwellings, offices, enterprise-wide computer networks, intranets, and the Internet.

For purposes of illustration, application programs and other executable program components such as the operating system 805 are illustrated herein as discrete blocks, although it is recognized that such programs and components can reside at various times in different storage components of the computing device 801, and are executed by the one or more processors 803 of the computer 801. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

For purposes of illustration, application programs and other executable program components are illustrated herein as discrete blocks, although it is recognized that such programs and components can reside at various times in different storage components. An implementation of the described methods can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A pressure sensor device for detecting pressure applied to a location on a person comprising:

a first circuit board;

a second circuit board;

a force sensing mechanism affixed to a center portion of a top surface of the first circuit board;

a turret pin mechanism affixed to a center portion of the second circuit board such that the turret pin mechanism is in line with a distal end of the force sensing mechanism, wherein the turret pin mechanism is configured to protrude a predetermined length above a top surface of the second circuit board and a predetermined length below a bottom surface of the second circuit board; and one or more pogo pins affixed to the top surface of the first circuit board and the bottom surface of the second circuit board, wherein the one or more pogo pins are configured to be connected between the first circuit board and the second circuit board.

2. The pressure sensor device of claim 1, wherein the first circuit board is configured into a circular structure, and wherein the second circuit board is configured into a circular structure.

3. The pressure sensor device of claim 1, wherein the first circuit board comprises an amplifier communicatively coupled to the force sensing mechanism.

4. The pressure sensor device of claim 1, wherein the first circuit board comprises a bottom printed circuit board (PCB) of the pressure sensor device and the second circuit board comprises a top PCB of the pressure sensor device.

5. The pressure sensor device of claim 1, wherein the one or more pogo pins are configured to lift the second circuit board such that the turret pin mechanism does not contact the force sensing mechanism when no pressure is applied to the pressure sensor device.

6. The pressure sensor device of claim 1, wherein the one or more pogo pins comprise one or more low-profile spring-loaded brass pogo pins.

7. The pressure sensor device of claim 1, wherein the one or more pogo pins are configured to be equidistantly spaced around a parameter of the first circuit board and the second circuit board.

8. The pressure sensor device of claim 1, wherein the force sensing mechanism comprises a capacitive pressure sensor or a piezoresistant sensor.

9. The pressure sensor device of claim 1, wherein the turret pin mechanism is configured to contact the force sensing mechanism when pressure is applied to the sensor device.

10. The pressure sensor device of claim 3, wherein the amplifier is affixed to the first circuit board.

11. The pressure sensor device of claim 3, wherein the force sensing mechanism is configured to generate an output voltage signal based on a pressure applied to the pressure sensor device.

12. The pressure sensor device of claim 11, wherein the output voltage signal is amplified by the amplifier.

13. The pressure sensor device of claim 1, wherein the pressure sensor device is configured to be embedded into an undergarment.

14. The pressure sensor device of claim 13, wherein the undergarment is configured to be worn underneath a compression garment.

15. The pressure sensor device of claim 1, further comprising a wireless communication module for transmitting sensor data.

16. The pressure sensor device of claim 1, further comprising a temperature sensor.

17. The pressure sensor device of claim 1, further comprising a humidity sensor.

18. The pressure sensor device of claim 2, wherein the first circuit board comprises identical dimensions of the second circuit board.

19. The pressure sensor device of claim 1, wherein the pressure sensor device comprises a thickness of less than 10 mm.

20. The pressure sensor device of claim 1, wherein the pressure sensor device is configured to transmit sensor data wirelessly using Bluetooth Low Energy (BLE) protocol.

* * * * *